(12) United States Patent
Walthall et al.

(10) Patent No.: US 12,053,409 B2
(45) Date of Patent: Aug. 6, 2024

(54) BODILY WASTE COLLECTION USING PERIODIC PRESSURE

(71) Applicant: PureWick Corporation, El Cajon, CA (US)

(72) Inventors: Jill M. Walthall, Avondale Estates, GA (US); Michael W. Drobnik, Downers Grove, IL (US); Christopher D. Drobnik, Wauconda, IL (US)

(73) Assignee: Pure Wick Corporation, Covington, GA (US)

( * ) Notice: Subject to any disclaimer, the term of this patent is extended or adjusted under 35 U.S.C. 154(b) by 175 days.

(21) Appl. No.: 17/412,864

(22) Filed: Aug. 26, 2021

(65) Prior Publication Data
US 2022/0062023 A1 Mar. 3, 2022

Related U.S. Application Data

(60) Provisional application No. 63/071,821, filed on Aug. 28, 2020.

(51) Int. Cl.
*A61F 5/445* (2006.01)
*A61F 5/44* (2006.01)
(Continued)

(52) U.S. Cl.
CPC ............ *A61F 5/445* (2013.01); *A61F 5/4404* (2013.01); *A61F 5/441* (2013.01); *A61M 1/75* (2021.05); *A61M 1/84* (2021.05)

(58) Field of Classification Search
CPC ............ A61F 5/44–4556; A61M 1/77; A61M 1/84–85; A61M 1/75; A61M 1/60;
(Continued)

(56) References Cited

U.S. PATENT DOCUMENTS 5,865,819 A * 2/1999 Cisko, Jr. ............... A61F 5/445
604/338
5,958,213 A 9/1999 Goto
(Continued)

FOREIGN PATENT DOCUMENTS

CN 106236363 A * 12/2016 ........... A61F 5/4404
CN 108354703 A * 8/2018 ............. A61F 5/445
(Continued)

OTHER PUBLICATIONS

U.S. Appl. No. 63/033,310, filed Jun. 2, 2020.
(Continued)

*Primary Examiner* — Rebecca E Eisenberg
*Assistant Examiner* — Linnae E. Raymond
(74) *Attorney, Agent, or Firm* — Dorsey & Whitney LLP

(57) ABSTRACT

Examples relate to systems and methods to periodically apply inward pressure against the contents of non-intrusive bodily waste collection devices. The systems and methods disclosed herein utilize a non-intrusive bodily waste collection device having an outermost fluid impermeable barrier forming a chamber therein, one or more ports on the fluid impermeable barrier for removing fluids therefrom via a vacuum source, and one or more input ports fluidly coupled to a positive pressure source to input fluid into the chamber to collectively apply periodic inward pressure against the contents of the bodily waste collection device.

18 Claims, 8 Drawing Sheets

(51) Int. Cl.
*A61F 5/441* (2006.01)
*A61M 1/00* (2006.01)
(58) Field of Classification Search
CPC ............ A61M 1/71; A61M 1/79; A61M 1/87; A61M 2202/0014; A61M 2202/068; A61M 2210/1067; A61G 9/02
See application file for complete search history.

(56) References Cited

U.S. PATENT DOCUMENTS

| | | | |
|---|---|---|---|
| 2009/0065412 | A1 | 3/2009 | Mbarki et al. |
| 2011/0137273 | A1 | 6/2011 | Muellejans et al. |
| 2012/0233762 | A1* | 9/2012 | Huang .................... A61F 5/451 4/462 |
| 2014/0276501 | A1 | 9/2014 | Cisko |
| 2017/0354906 | A1 | 12/2017 | Wu |
| 2021/0188680 | A1 | 6/2021 | Kumkrong et al. |
| 2021/0330485 | A1 | 10/2021 | Sexton et al. |
| 2022/0062023 | A1 | 3/2022 | Walthall et al. |
| 2022/0287867 | A1 | 9/2022 | Jones et al. |
| 2022/0379001 | A1* | 12/2022 | Sharma ................. A61F 5/4405 |
| 2023/0293336 | A1 | 9/2023 | Sexton et al. |

FOREIGN PATENT DOCUMENTS

| | | | | |
|---|---|---|---|---|
| CN | 108852605 A | * | 11/2018 | ........... A61F 5/4404 |
| DE | 79818 C | | 10/1893 | |
| WO | WO-0239937 A1 | * | 5/2002 | ............. A61F 5/451 |
| WO | 2007134608 A2 | | 11/2007 | |
| WO | 2017001846 A1 | | 1/2017 | |
| WO | WO-2019239433 A1 | * | 12/2019 | |

OTHER PUBLICATIONS

U.S. Appl. No. 63/071,821, filed Aug. 28, 2020.
U.S. Appl. No. 63/088,539, filed Oct. 7, 2020.
U.S. Appl. No. 63/159,280, filed Mar. 10, 2021.
International Search Report and Written Opinion from International Application No. PCT/US2021/035181 mailed Sep. 16, 2021.
Non-Final Office Action for U.S. Appl. No. 17/494,578 mailed Mar. 2, 2023.
Non-Final Office Action for U.S. Appl. No. 17/654,156 mailed Apr. 10, 2023.
U.S. Appl. No. 17/494,578, filed Oct. 5, 2021.
U.S. Appl. No. 17/654,156, filed Mar. 9, 2022.
U.S. Appl. No. 17/999,648, filed Nov. 22, 2022.
Issue Notification for U.S. Appl. No. 17/494,578 mailed Nov. 22, 2023.
Notice of Allowance for U.S. Appl. No. 17/654,156 mailed Aug. 29, 2023.
Notice of Allowance for U.S. Appl. No. 17/654,156 mailed Dec. 14, 2023.

* cited by examiner

BODILY WASTE COLLECTION USING PERIODIC PRESSURE

CROSS REFERENCE TO RELATED APPLICATIONS

This application claims priority to U.S. Provisional Application No. 63/071,821 filed on 28 Aug. 2020, the disclosure of which is incorporated herein in its entirety by this reference.

BACKGROUND

An individual may have limited or impaired mobility such that bowel movements in a restroom are challenging or impossible. For example, the individual may have a condition, had a surgery, or a have disability that impairs mobility. In another example, the individual may have restricted travel conditions such as those experience by pilots, drivers, and workers in hazardous areas. Additionally, stool collection from the individual may be needed for monitoring purposes or clinical testing.

Bed pans and ostomy bags, may be used to address some of these circumstances. However, bed pans and ostomy bags have several problems associated therewith. For example, bed pans may be prone to discomfort, spills, and other hygiene issues. Ostomy bags require intrusive surgery. For example, using ostomy bags requires a surgical procedure to make an ostomy and stoma to connect to the ostomy bag, which may be painful, prone to infections, and leave permanent scarring or other side effects.

Thus, users and manufacturers of stool collection devices continue to seek new and improved devices, systems, and methods to collect stool.

SUMMARY

Embodiments disclosed herein are related to systems and methods of using non-intrusive bodily waste collection devices to periodically apply inward pressure to the contents thereof. In an embodiment, a bodily waste collection system is disclosed. The bodily waste collection system includes a fluid storage container configured to hold a fluid. The bodily waste collection system includes a bodily waste collection device fluidly coupled to the fluid storage container, the bodily waste collection device having a chamber configured to be fluidly connected with an anus or stoma of a wearer. The bodily waste collection system includes a drainage tubing in fluid communication with the chamber. The bodily waste collection system includes a vacuum source fluidly coupled to one or more of the fluid storage container or the bodily waste collection device via the drainage tubing, the vacuum source configured apply a vacuum to draw fluid from the chamber via the drainage tubing. The bodily waste collection system includes a positive pressure source in fluid communication with the chamber, wherein the positive pressure source is configured to periodically input fluid into the chamber to create periodic pressure in the chamber in combination with the vacuum. The bodily waste collection system includes one or more input tubes fluidly connecting the chamber with the positive pressure source.

In an embodiment, a method to collect bodily waste is disclosed. The method includes positioning an opening of a bodily waste collection device over an anus or stoma of a wearer, the bodily waste collection device having a chamber configured to be fluidly connected with an anus or stoma of a wearer. The method includes receiving waste from the anus or stoma into the chamber. The method includes applying a vacuum to the chamber. The method includes periodically inputting a fluid into the chamber to at least partially inflate the bodily waste collection device.

In an embodiment, a bodily waste collection system is disclosed. The bodily waste collection system includes a fluid storage container configured to hold a fluid. The bodily waste collection system includes a bodily waste collection device fluidly coupled to the fluid storage container. The bodily waste collection device includes an annular body defining an opening therein, the annular body being configured to be positioned over an anus or stoma of the wearer to position the opening around the anus or the stoma. The bodily waste collection device includes a fluid impermeable barrier affixed to the annular body, the fluid impermeable barrier having an outer surface and an inner surface, the inner surface at least partially defining a chamber within the fluid impermeable barrier. The bodily waste collection device includes a filter bag disposed within the chamber and positioned to receive waste via the opening. The bodily waste collection device includes one or more ports disposed on the fluid impermeable barrier. The bodily waste collection system includes a drainage tubing in fluid communication with the chamber via the one or more ports. The bodily waste collection system includes a vacuum source fluidly coupled to one or more of the fluid storage container or the bodily waste collection device via the drainage tubing, the vacuum source being configured apply a vacuum to draw fluid from the chamber via the drainage tubing. The bodily waste collection system includes a positive pressure source in fluid communication with the chamber, wherein the positive pressure source is configured to periodically input fluid into the chamber to create periodic pressure in the chamber in combination with the vacuum. The bodily waste collection system includes one or more input tubes fluidly connecting the chamber with the positive pressure source. The bodily waste collection system includes a controller operably coupled to the positive pressure source and the vacuum source, wherein the controller is configured to selectively control the positive pressure source to periodically input fluid into the chamber, and to control application of vacuum by the vacuum source, to create periodic pressure within the bodily waste collection device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to devices, systems, and methods of using bodily waste collection devices. The systems and methods of disclosed herein utilize a non-intrusive bodily waste collection device having a chamber therein, a vacuum source fluidly connected to the chamber, and a positive pressure source connected to the chamber. The vacuum source and the positive pressure source are utilized to control the pressure inside of the chamber to periodically apply inward pressure to the contents in the chamber. Accordingly, contents (e.g., bodily waste) of the chamber may be subjected to periodic inward pressure by the fluid impermeable barrier of the bodily waste collection device.

The bodily waste collection device may have an outermost fluid impermeable barrier forming a chamber therein, a filter bag disposed in the chamber, an annular body defining an opening into the chamber and that is sized and shaped to interface with a wearer's anus or stoma, and one or more ports on the fluid impermeable barrier for removing fluids therefrom. The waste is received into filter bag via the opening. Gravity and/or suction pull fluid from the waste which passes through the filter bag while the solids of the waste are retained in the filter bag. The fluid moves to a gravimetrically low portion or lowest pressure portion of the chamber or to a vacuum applied in the chamber. The fluid is removed via one or more ports fluidly coupled to one or more of a fluid storage container or the vacuum source.

By applying the periodic inward pressure, the liquid may be forced from the bodily waste and the bodily waste may be moved in the chamber thereby filtering the fluid from the waste and retaining the solids in the filter bag. The systems and methods disclosed herein preventing clogging of drainage tubing, allow longer use of waste collection devices by reducing the volume of waste therein, move the waste away from the opening toward a distal end of the chamber, and allow waste content monitoring. The bodily waste collection systems and methods are particularly effective for collecting semi-solid stool or liquid stool (e.g., diarrhea).

Figure 1:
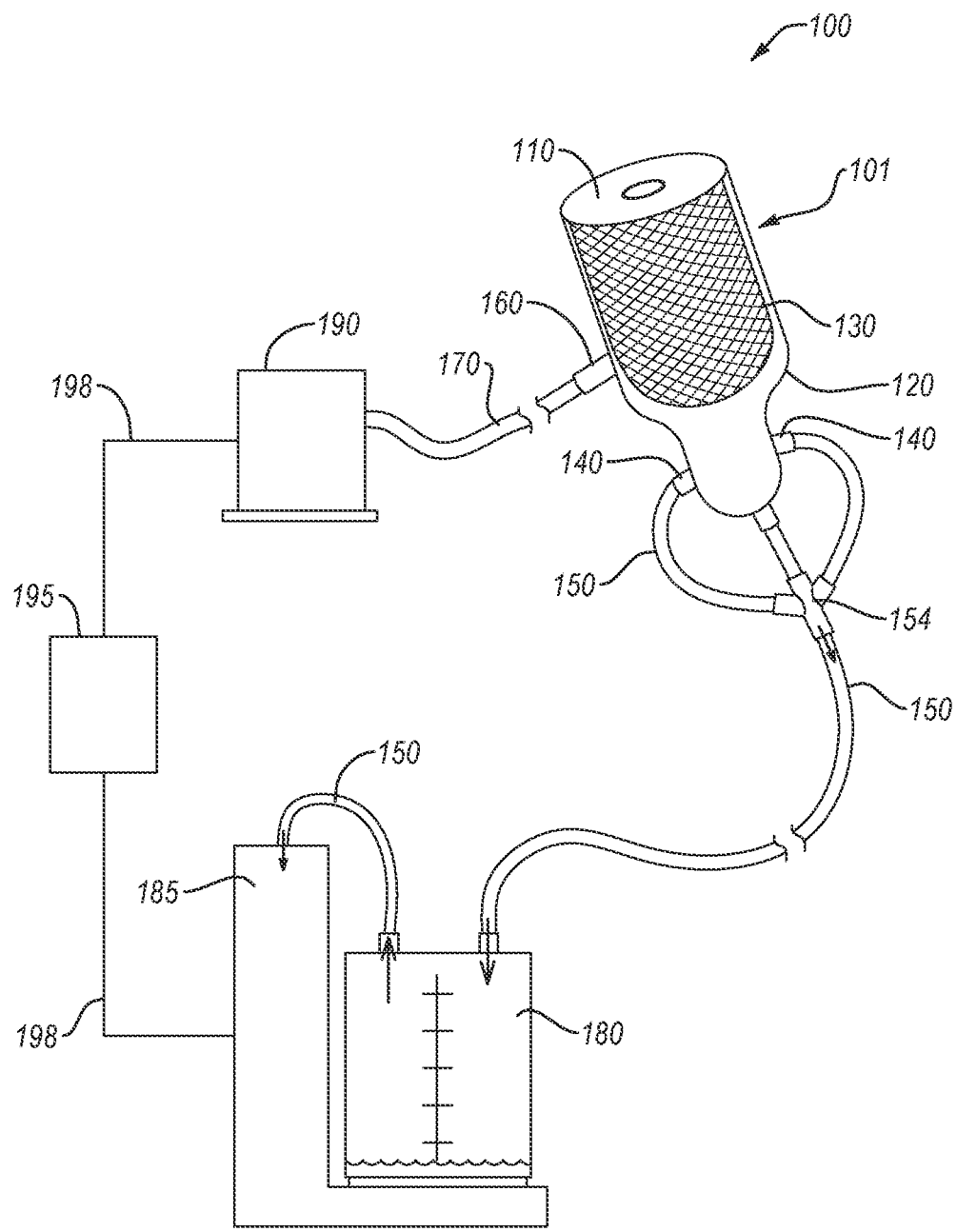
FIG. 1 is a schematic of a bodily waste collection system, according to an embodiment.

The bodily waste collection devices disclosed herein may be used in a system for collecting bodily waste. FIG. 1 is a schematic of a bodily waste collection system 100, according to an embodiment. The system 100 includes a bodily waste collection device 101, a fluid storage container 180, a vacuum source 185, and a positive pressure source 190. The bodily waste collection device 101 may be fluidly coupled to one or more of the fluid storage container 180 or the vacuum source 185 via drainage tubing 150. The bodily waste collection device 101 (e.g., chamber) may be fluidly coupled to the positive pressure source 190 via at least one input tube 170. The system 100 may include a controller 195 to selectively control operation of the vacuum source 185 and the positive pressure source 190 to produce periodic (inward) pressure in the bodily waste collection device 101.

The bodily waste collection device 101 may be similar or identical to any of the bodily waste collection devices disclosed herein, in one or more aspects. For example and as explained in more detail below, the bodily waste collection device 101 may include an annular body 110, a fluid impermeable barrier 120, a filter bag 130, one or more ports 140, and at least one input port 160.

Figure 2:
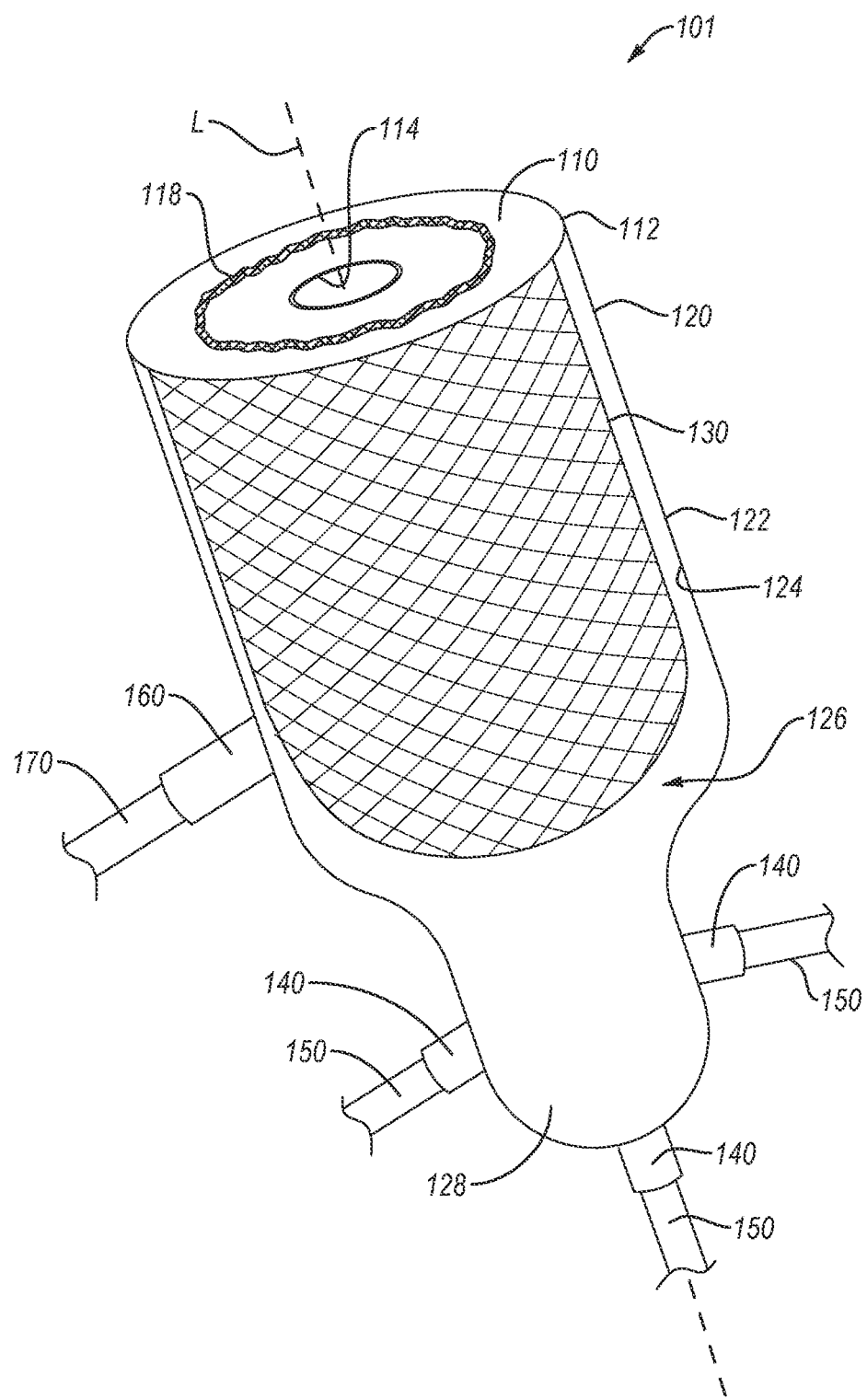
FIG. 2 is an enlarged, isometric view of the bodily waste collection device, according to an embodiment.

FIG. 2 is an enlarged, isometric view of the bodily waste collection device 101, according to an embodiment. The bodily waste collection device 101 includes the annular body 110, the fluid impermeable barrier 120 forming a chamber 126 therein, the filter bag 130 disposed within the chamber 126, and one or more ports 140 disposed on the fluid impermeable barrier 120. The device 101 is configured to be attached to a wearer to collect the waste from the wearer and remove liquids from the waste. The annular body 110 is attached to the wearer around the wearer's anus or stoma to position the device 101 for use. Waste enters the chamber 126 via an opening 114 in the annular body 110, the filter bag 130 in the chamber 126 filters the solids from the waste and allows the fluids to pass therethrough, the liquid moves to a gravimetrically low point of the chamber 126 and is removed therefrom, such as via vacuum.

The annular body 110 includes a thin interfacing layer 112 having the opening 114 therein. The annular body 110 may be a complete or partial annulus. For example, the annular body 110 may be a disc-shaped body with a hole therein. In some examples, the annular body 110 may include a flat sheet of material with a hole located at or near an edge of the material to form a partial annulus. The interfacing layer 112 is fluid impermeable. For example, the interfacing layer may include a polymer, silicone, or the like. The interfacing layer 112 may be constructed of a smooth and/or soft material such as a closed cell foam, silicon, a smooth plastic, or may include an outwardly facing layer of relatively smooth material and/or soft material (e.g., silicone). The interfacing layer 112 may be an annular disc, sheet, plate, or other body having the opening 114 within an outermost periphery thereof. The interfacing layer 112 is sized and shaped to fit within the intergluteal cleft of a wearer, such as when bent, folded or otherwise manipulated.

The annular body 110 (interfacing layer 112) may be bendable to comply to pressure applied thereto, such as from a wearer or medical professional. The annular body 110 may be composed of a material and have a thickness that allows the annular body 110 to bend responsive to external forces, without breaking. For example, the interfacing layer 112 may be deformable responsive to bending forces. The interfacing layer 112 may be deformed to complement the anatomy (e.g., anatomical features) of a wearer, such as to fit within the intergluteal cleft. Accordingly, the annular body 110 may be compliant for folding, bending, or the like. A medical professional or a wearer may fold and/or bend the annular body 110 in half to insert the annular body between the buttocks of the wearer to be disposed within the intergluteal fold during use. Such a fold may form a cusp, having at least a portion of the opening 114 therein. Accordingly, the annular body 110 may be provided as a generally planar body, a bent body, or a folded body. By folding or bending the annular body 110, a wearer or user (e.g., medical professional) may non-intrusively position the opening 114 at least partially around the anus or a stoma of a wearer.

The opening 114 may be disposed within the outer periphery of the interfacing layer 112. As shown, the opening 114 may be disposed at or near a centroid of the interfacing layer 112. In some examples, the opening 114 may be disposed closer to the outer periphery of the interfacing layer 112 than illustrated. The opening 114 is sized and shaped to fit around (e.g., over) the anus or stoma of the patient without occluding the stoma or anus. For example, the opening 114 may be circular, elliptical, rectangular, or any other shape. Accordingly, the annular body 110 is sized and shaped to be positioned over an anus or stoma of a wearer to position the opening 114 around the anus or stoma. Waste may be passed into the bodily waste collection device 101 via the opening 114.

The interfacing layer 112 of the annular body 110 may include an adhesive 118 thereon to adhere to the skin of a subject, such as within the intergluteal cleft. The adhesive 118 may be integrally formed in or disposed on an outward facing surface of the interfacing layer 112. Such adhesive 118 may secure the bodily waste collection device 101 in position such that the opening 114 is maintained around or at least proximate to the anus or stoma of the wearer. The adhesive 118 may be disposed at one or more points between the opening 114 and the outer periphery of the annular body 110. The adhesive 118 may include a medical adhesive or any other adhesive that is safe to use against the skin of humans, such as acrylate adhesives (e.g., methacrylates, epoxy diacrylates, or cyanoacrylate adhesives), silicone adhesives, hydrogels, or the like.

While shown as a substantially continuous ring on the interfacing layer 112, the adhesive 118 may be disposed on the interfacing layer 112 as one or more spots, dots, or strips. The adhesive 118 may be disposed on the interfacing layer 112 as one or more rings of adhesive extending around the opening 114. In some examples (not shown), substantially the entire interfacing layer 112 may be covered by adhesive 118.

The fluid impermeable barrier 120 is attached to the annular body 110 to at least temporarily retain received bodily waste therein and prevent leakage to the outside environment. The fluid impermeable barrier 120 includes an open mouth at a first (e.g., upper) end and a closed second (e.g., lower) end. The first end is bound to the annular body 110 and the second end forms the sump of the fluid impermeable barrier 120.

The fluid impermeable barrier 120 is formed from a fluid impermeable material, such as portions (e.g., layers) including a polymer, a metal film, rubber, or the like. For example, the fluid impermeable barrier 120 may include silicone, polypropylenes, polyethylenes, polyethylene terephthalates, polystyrenes, polyurethanes, polycarbonates, polyamides, polyesters, polyacrylates, polychloroprene, vinyl, polyvinyl chloride, poly(vinyl imidazole), latex, silanes (e.g., an halogenated alkyl silane), perfluorinated polymers, polytetrafluoroethylene (PTFE), chlorosulphonate polyolefins, polyethylene oxide, blends or copolymers of any of the foregoing, or any other fluid impermeable polymer.

The fluid impermeable barrier 120 may be transparent in one or more portions thereof. The fluid impermeable barrier 120 may be translucent or opaque in one or more portions thereof. For example, the fluid impermeable barrier 120 may include a transparent window around the filter bag or in a lower portion of the fluid impermeable barrier 120 to allow a user or wearer to monitor waste and liquids therein.

The fluid impermeable barrier 120 includes an outer surface 122 and an inner surface 124. The outer surface 122 may be relatively smooth or soft to prevent sores or discomfort for the wearer. The inner surface 124 defines a chamber 126. The chamber 126 receives and retains the bodily waste therein. Liquid from the bodily waste may travel through the chamber 126 from the upper region of the chamber 126 at the first end to a lower region (e.g., gravimetrically low point) of the chamber 126 at the second end.

The mouth of the fluid impermeable barrier 120 is mated to the annular body 110, such as at the outer periphery of the annular body 110. Accordingly, waste received into the bodily waste collection device 101 enters the chamber 126 via the opening 114 of the annular body 110 mated to the fluid impermeable barrier 120. The mouth of the fluid impermeable barrier 120 may be mated to the annular body 110 at the outer periphery of the annular body 110, at one or more points internal to the outer periphery such as at the inner periphery of the annular body 110 (e.g., opening 114), or any points between the outer periphery and the opening 114.

The mouth of the fluid impermeable barrier 120 may be adhered, welded, or otherwise affixed to the annular body 110. At least a portion of the fluid impermeable barrier 120 (e.g., mouth of the fluid impermeable barrier 120) may be integrally formed with the annular body 110, such as having a one-piece construction. In such examples, one or more portions of the fluid impermeable barrier may be open as initially formed, and later sealed after the filter bag is installed.

The fluid impermeable barrier 120 may have a substantially cylindrical or conical shape. For example, the fluid impermeable barrier 120 may include an upper portion having a greater outer dimension than a lower portion of the fluid impermeable barrier 120. The fluid impermeable barrier 120 may be shaped as a pouch having opposing sides that are joined along the edges thereof. In some examples, the fluid impermeable barrier 120 may include a sump 128 in a portion of the fluid impermeable barrier 120 intended to be positioned at the gravimetrically low portion of device 101 during use. The sump 128 may include a portion of the fluid impermeable barrier 120 sized and shaped to direct the fluid in the chamber to one or more ports 140 disposed on the fluid impermeable barrier 120 in the sump 128. For example, the sump 128 may include a narrower portion of the chamber 126 than an upper portion. The sump 128 may be a side channel or pocket in the chamber 126, a conical shaped terminus of the chamber 126, or the like.

The bodily waste collection device 101 includes the filter bag 130 disposed within the chamber 126, and positioned to receive waste via the opening 114 of the annular body 110. The filter bag 130 may have a length that is shorter than a length of the fluid impermeable barrier 120. Accordingly, the bottom of the filter bag 130 does not extend to the bottom of the fluid impermeable barrier 120. The filter bag 130 may be substantially cylindrical with a closed bottom substantially opposite to the mouth of the filter bag 130. In some examples, the filter bag is conically shaped. In some examples, the filter bag 130 is configured as or shaped like a pouch.

The filter bag 130 may include a bag or pouch constructed of a mesh material. The mesh material has a sieve size selected to allow fluids to pass therethrough and retain solids therein. The sieve size (e.g., mesh size) may include at least about A five micrometer (μm) mesh, such as about 5 μm to about 1,500 μm, about 100 μm to about 1000 μm, about 250 μm to about 500 μm, about 500 μm to about 1,000 μm, less than about 1,500 μm, less than about 1,000 μm, less than about 800 μm, less than about 400 μm, or larger than about 100 μm. The filter bag 130 may be seamless. The filter bag 130 may include one or more layers of mesh material, such as a single layer or dual layers.

The mesh material may include fibers of a polymer or natural material. For example, the mesh material may include fibers of a polymer, such as nylon, polypropylenes, polyethylenes, polyethylene terephthalates, polystyrenes, polyurethanes, polycarbonates, polyamides, polyesters, polyacrylates, polychloroprene, vinyl, polyvinyl chloride, poly(vinyl imidazole), latex, silanes (e.g., an halogenated alkyl silane), perfluorinated polymers, polytetrafluoroethylene (PTFE), chlorosulphonate polyolefins, polyethylene oxide, blends or copolymers of any of the foregoing. The mesh may be formed of natural fibers such as cotton (e.g., cheesecloth). The mesh material may be woven or non-woven. The mesh material may be a felt of any of the materials disclosed above.

The filter bag 130 may be affixed the annular body 110 or the fluid impermeable barrier 120. For example, the filter bag 130 may be affixed to the annular body 110 between the opening 114 and the outer periphery thereof. By spacing the filter bag 130 from the fluid impermeable barrier 120, a space is created between the filter bag and the fluid impermeable barrier to allow the liquid to separate from the solids in the bodily waste, no matter the orientation of the wearer. A mouth of the filter bag 130 may be bound to the underside of the annular body 110 such that the opening 114 is contained within the filter bag 130. The mouth of the filter bag 130 may be bound to the annular body 110 to encircle the opening 114. Put another way, waste passed into the opening 114 may be disposed within the filter bag 130 first. The mouth of the filter bag 130 may be bound to the underside of the annular body 110 by adhesive (e.g., any adhesive), stitching, heat welding, staples, integral formation, or the like.

The filter bag 130 may be affixed to the annular body 110 at least proximate to the opening 114. For example, the filter bag 130 may be adhered, sewn, stapled, or otherwise attached to the annular body at the opening 114. The filter bag 130 may be affixed to the annular body 110 at an outer periphery of the annular body 110. In some examples, the filter bag 130 is affixed to the top of the annular body 110 (e.g., at the outwardly facing portion of the interfacing layer 112), such as by extending out of the chamber 126 from the opening 114. In some examples, the bodily waste collection device 101 may not include the filter bag.

The bodily waste collection device 101 includes the one or more ports 140. The one or more ports 140 provide a passageway to fluidly connect the chamber 126 with one or more of the drainage tubing 150, a vacuum source, or fluid storage container. The one or more ports 140 are disposed on the fluid impermeable barrier 120. The one or more ports 140 may be positioned in locations at or near where liquid is expected to collect in the chamber 126. For example, the one or more ports 140 may be positioned on the fluid impermeable barrier 120 in locations expected to be at or near a gravimetrically low point of the fluid impermeable barrier 120 during use, such as when a wearer is sitting, laying, reclined, standing, or in any other position. The one or more ports 140 may be positioned in the lower portion of the fluid impermeable barrier 120 at the sump 128. Any number of ports may be used. For example, at least one port or at least 2 ports may be disposed in the fluid impermeable barrier 120.

The one or more ports 140 are sized and shaped to connect to drainage tubing 150 (or tube) to remove fluids collected in the chamber 126. For example, the one or more ports 140 are in fluid communication with the chamber 126 and are used to place the drainage tubing 150 in fluid communication with the chamber 126, such as to remove fluids therefrom. The one or more ports 140 may be sized and shaped to receive the drainage tubing 150 therein, such as being a female connection. The female connection may be sized and shaped to allow the drainage tubing 150 to insert therein. The one or more ports 140 may be configured to receive the drainage tubing 150 thereon, such as being a male connection (e.g., nipple or tube connection). When the drainage tubing 150 is connected to the one or more ports 140, the drainage tubing 150 fluidly couples the chamber 126 to one or more of a storage container or vacuum source via the one or more ports 140.

The drainage tubing 150 (e.g., drainage tube) may include medical tubing. For example, the drainage tubing 150 may be constructed of one or more polymers such as silicone, latex, ethylene vinyl acetate (EVA), polytetrafluoroethylene (PTFE), silicone polyurethane, polyamide, polyurethane, polyethylene, other thermoplastics and block copolymers thereof, or any other suitable polymers for medical use. The fluids may be drained from the chamber 126 via the one or more ports 140 fluidly coupled to the drainage tubing 150, such as via gravity, a vacuum force, or any other force.

The bodily waste collection device 101 may include at least one input port 160. The at least one input port 160 may be similar or identical to the at least one port 140 in one or more aspects. The at least one input port 160 may be sized and shaped to connect to one or more input tubes 170. The one or more input tubes 170 may be similar or identical to the drainage tubing 150 in one or more aspects. The one or more input tubes 170 may be operably coupled to the positive pressure source 190 such as an air or liquid pump. The one or more input tubes 170 may input air or a liquid into the chamber 126 such as to at least partially inflate the bodily waste collection device 101, to prevent suction from the ports 140 from reaching the wearer, or both. The one or more input tubes 170 may be used to input a liquid or gas into the bodily waste collection device 101 (e.g., into one or more bladders therein), such as water to selectively provide inward pressure to the contents of the chamber 126. At least one input port 160 may be positioned nearer the annular body 110 than the one or more ports 140, such as in an upper portion of the fluid impermeable barrier (e.g., proximate to the annular body 110). In such examples, the at least one input port 160 may be used to at least partially inflate the chamber 126 to allow the input fluid(s) to be input between the suction applied at the one or more ports 140 and the wearer, or both.

In some examples (not shown), a first input port 160 may be positioned proximate to the annular body 110 and at least a second input port 160 may be positioned in a medial or distal portion (relative to the annular body 110) of the fluid impermeable barrier 120. In such examples, the fluid (e.g., air) input into the first input port 160 may prevent the vacuum from reaching the wearer and the fluid input into the at least a second input port 160 may inflate the fluid impermeable barrier 120.

In some examples, the one or more input tubes 170 may be utilized to selectively input the fluid(s) into the chamber 126 to selectively inflate the bodily waste collection device 101. Accordingly, as the vacuum is constantly or alternately applied in the chamber 126 by the vacuum source 185, the bodily waste collection device 101 may be periodically inflated between application of vacuum and inward force against the bodily waste therein. Such pseudo-peristaltic pressure may be utilized to more effectively remove liquid from the bodily waste and to move the bodily waste toward the distal end of the bodily waste collection device 101.

The bodily waste collection device 101 may include one or more vents or one-way valves on the fluid impermeable barrier 120. Such one-way valves may be sized and shaped to open inwardly toward the chamber 126 responsive to a vacuum force applied thereto. Accordingly, vacuum applied in the chamber 126 may be at least partially prevented from reaching the wearer.

Returning to FIG. 1, the drainage tubing 150 may be fluidly coupled to the fluid storage container 180, such as via the one or more ports 140. Drainage tubing 150 may be similar or identical to any of the drainage tubing disclosed herein, in one or more aspects. The fluids (e.g., liquid from bodily waste) may be removed from the chamber of the bodily waste collection device 101 via the drainage tubing 150 and one or more ports 140. The fluid may travel through the drainage tubing 150 to the fluid storage container 180, such as via vacuum force. The drainage tubing 150 from multiple ports 140 may be joined into single piece of drainage tubing 150 via a manifold 154 (e.g., junction connection). The manifold 154 may include male or female connections for mating to the drainage tubing 150.

Fluid storage container 180 may include a bag (e.g., drainage bag), a bottle or canister (e.g., collection jar), or any other enclosed container for storing bodily fluids. The vacuum source 185 may be fluidly coupled to one or more of the fluid storage container or the bodily waste collection device via the drainage tubing 150. The vacuum source 185 may apply a vacuum to directly or indirectly draw fluid from the chamber of the bodily waste collection device 101 via the drainage tubing 150. For example, the vacuum source 185 may provide a vacuum for pulling fluids from the bodily waste collection device 101 into the fluid storage container 180. The fluid collected from the bodily waste collection device 101 is moved through the drainage tubing 150 into the fluid storage container 180. By having a separate connection to the vacuum source 185 on the fluid storage container 180, the fluids removed from the bodily waste collection device 101 may be prevented from entering the vacuum source 185.

The vacuum source 185 may include one or more of a manual vacuum pump, an electric vacuum pump, a diaphragm pump, a centrifugal pump, a displacement pump, a magnetically driven pump, a peristaltic pump, or any pump configured to produce a vacuum. The vacuum source 185 may include a wall mounted suction line, such as found in a hospital room. The vacuum source 185 provides a vacuum or suction to remove fluid from the bodily waste collection device 101. In examples, the vacuum source 185 may be powered by one or more of a power cord (e.g., connected to a power socket), one or more batteries, or even manual power (e.g., a hand operated vacuum pump). The vacuum source 185 may include one or more of a switch, a button, a plug, a remote, or any other actuator suitable to activate the vacuum source 185. The vacuum source 185 may be selectively operated by a user (e.g., medical personnel, the wearer, or a caretaker), such as directly on the vacuum source or via the controller 195.

The bodily waste collection device 101 may be operably coupled to the positive pressure source 190 via the input port 160 and the one or more input tubes 170. The positive pressure source 190 may be used to input one or more fluids into the chamber of the bodily waste collection device 101. For example, the positive pressure source 190 (e.g., gas or air source) may be used to periodically input fluid into the chamber to create periodic pressure in the chamber in combination with the vacuum applied by the vacuum source 185. The positive pressure source 190 may include one or more of an air pump, a compressed air line, an oxygen source (e.g., compressed oxygen), a nitrogen source (e.g., compressed nitrogen), or any other source of gas. The positive pressure source 190 may include one or more of a liquid source such as a water line, water pump, a saline pump, or the like. The positive pressure source 190 may be used to selectively input a gas (e.g., air) into the chamber of the bodily waste collection device 101, such as to at least partially inflate the bodily waste collection device 101; to prevent suction applied therein from collapsing the chamber or reaching the wearers skin, anus, or stoma; or both. The positive pressure source 190 may be used to selectively input a liquid (e.g., saline) into the chamber of the bodily waste collection device 101 to clean the chamber or flush the chamber. In some examples, the positive pressure source 190 may include an air pump, a compressor, an air line (e.g., in a hospital room), or the like. An electronically controlled valve may be disposed between the positive pressure source 190 and the fluid impermeable barrier 120, to control the feed of air into the chamber 126. In some examples, the positive pressure source 190 may include a liquid (e.g., water) pump, a water line, or the like. In examples, where the fluid includes a liquid, the positive pressure source 190 may include a heater or temperature control component to control the temperature of the liquid pumped into the bodily waste collection device 101.

In some examples, the positive pressure source 190 and the vacuum source 185 may be located in a single device, such as a combination pump, diaphragm pump, or any other pump capable of creating a vacuum and pressurized air.

The controller 195 may be operably coupled to the vacuum source 185 or the positive pressure source 190 via connections 198, which may include hardwired connections or wireless connections (e.g., RF, Wi-Fi, Bluetooth®, etc.). The controller 195 may be utilized to control application of vacuum or fluid input into the bodily waste collection device 101. For example and as discussed in more detail below, the controller 195 may include machine readable and executable instructions for selectively controlling the timing, magnitude, and duration of vacuum force and/or fluid input into the bodily waste collection device 101 from the vacuum source 185 or the positive pressure source 190. A processor in the controller 195 may execute the instructions.

The controller 195 may include instructions to cause the vacuum source 185 to intermittently apply vacuum into the chamber, such as at least every 2 hours, at least every hour, at least every 30 minutes, at least every 20 minutes, at least every 15 minutes, at least every 10 minutes, at least every 5 minutes, or at least every 3 minutes. The controller 195 may include instructions to cause the vacuum source 185 to provide vacuum for a duration of at least 10 seconds, such 10 seconds to 1 minute, 1 minute to 3 minutes, 2 minutes to 5 minutes, or 5 minutes to 10 minutes, 5 minutes to 15 minutes, or 15 minutes to 30 minutes. The controller 195 may include instructions to cause the vacuum source 185 to intermittently apply vacuum into the chamber when the positive pressure source 190 is not providing input into the chamber.

The controller 195 may include instructions to cause the positive pressure source 190 to periodically input fluid into the chamber (e.g., provide fluid via the one or more input tubes), such as at least once every 3 hours, at least once an hour, at least every 30 minutes, at least every 20 minutes, at least every 15 minutes, at least every 10 minutes, at least every 5 minutes, or at least every 3 minutes. The controller 195 may include instructions to cause the positive pressure source 190 to provide input for a duration of at least 1 second, such as 1 second to 10 minutes, 5 seconds to 5 minutes, 10 seconds to 1 minute, 1 minute to 3 minutes, 2 minutes to 5 minutes, or 5 minutes to 10 minutes.

In practice, the vacuum source 185 and the positive pressure source 190 may be used to produce intermittent application of inward pressure to the contents of the bodily waste collection device 101. As the vacuum source 185 applies vacuum in the bodily waste collection device 101 the fluid impermeable barrier 120 may be pulled inward to apply inward pressure on the bodily waste therein. As the fluid is input into the bodily waste collection device 101 by the positive pressure source 190, the bodily waste collection device 101 may at least partially inflate thereby relieving the pressure on the bodily waste therein. By cycling at least the fluid input from the positive pressure source 190, cyclical inward pressure may be applied to help move the bodily waste in the bodily waste collection device 101 to remove liquid therefrom. Accordingly, the intermittent inward pressure may at least partially mimic peristalsis to help move the solids in bodily waste deposited in the bodily waste collection device to advance the bodily waste toward a distal end (e.g., sump) of the bodily waste collection device (e.g., opposite the opening 114).

Figure 3:
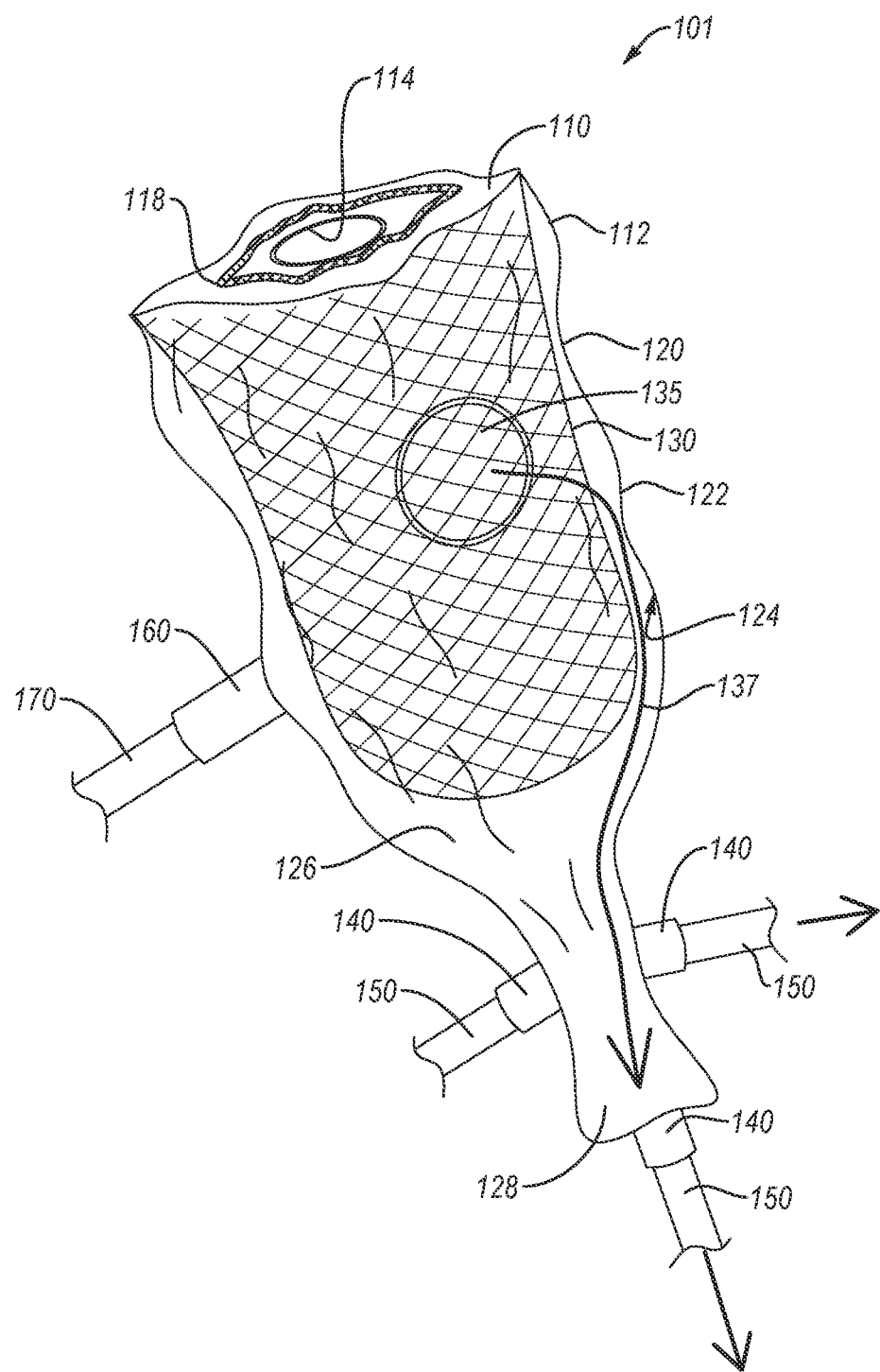
FIG. 3 is an isometric view of the bodily waste collection device of FIG. 2 under vacuum.

FIG. 3 is an isometric view of the bodily waste collection device 101 of FIG. 2 under vacuum. The bodily waste collection device 101 is placed under vacuum via vacuum force applied through the one or more ports 140. As the negative pressure builds in the chamber 126, the fluid impermeable barrier 120 moves inward toward the contents (e.g., filter bag 130) and bodily waste 135 therein. The bodily waste 135 may be semi-solid or liquid waste (e.g., diarrhea). Liquid 137 is removed from the bodily waste 135 via one or both of gravity or vacuum force. The filter bag 130 retains any solids from the bodily waste 135. By providing inward force against the bodily waste 135, more liquid 137 may be separated from the waste than if only gravity or vacuum is applied to the bodily waste 135. Additionally, by applying inward pressure to the bodily waste 135 with the inner surface 124 of the fluid impermeable barrier 120, the bodily waste 135 may be advanced through the chamber 126 from the opening 114 toward the sump 128.

Figure 4:
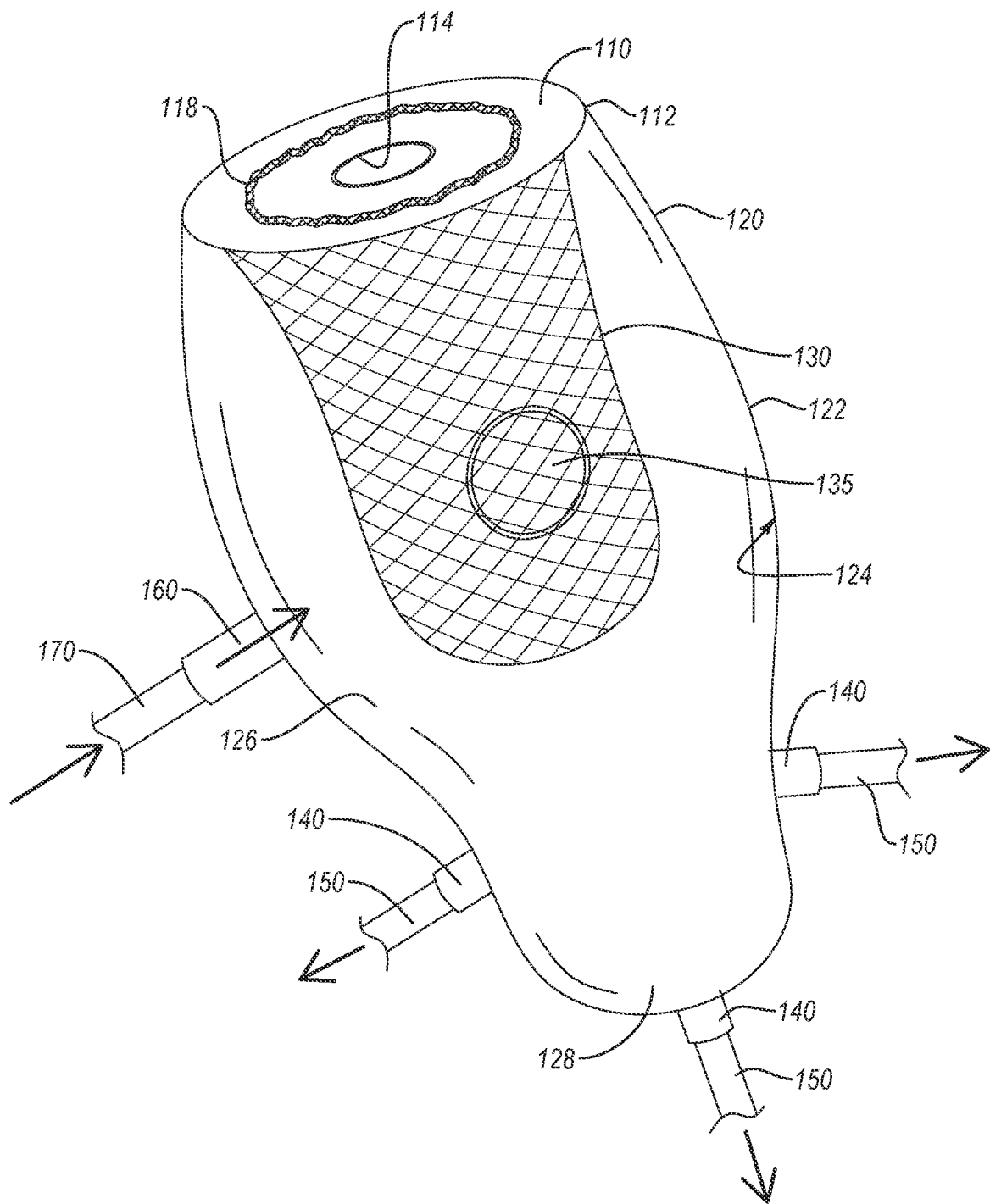
FIG. 4 is an isometric view of the bodily waste collection device of FIG. 2, with fluid input from the one or more input ports.

FIG. 4 is an isometric view of the bodily waste collection device 101 of FIG. 2 with fluid input from the one or more input ports 160. The fluid (e.g., air) input into to the chamber 126 may at least partially inflate the fluid impermeable barrier 120, thereby removing the inward pressure on the contents of the fluid impermeable barrier 120. As the inward pressure is released, or in the absence of the inward pressure, the bodily waste 135 may be pulled toward the second end region (e.g., the sump 128) of the chamber 126. During input of the fluid, the vacuum applied via the one or more ports 140 may be maintained or may be discontinued.

Liquid may continue to drain from the bodily waste 135 after the inward pressure is released. Accordingly, the vacuum may continue to remove liquid from the waste when the inward pressure is released. The vacuum may be terminated to allow the fluid impermeable barrier 120 to inflate faster if desired. After at least partial inflation, the input may be terminated and the vacuum may pull the fluid out of the chamber 126 to cause the inner surface of the fluid impermeable barrier to apply inward pressure against the bodily waste 135. By cyclically applying and relieving inward pressure, the liquid may be removed from the bodily waste 135 and the bodily waste 135 may be moved from the first end region (e.g., opening) toward the second end region (e.g., sump). The positive pressure source may periodically input fluid into the chamber to create periodic pressure (e.g., pseudo-peristaltic motion) in the chamber in combination with the vacuum.

Figure 5:
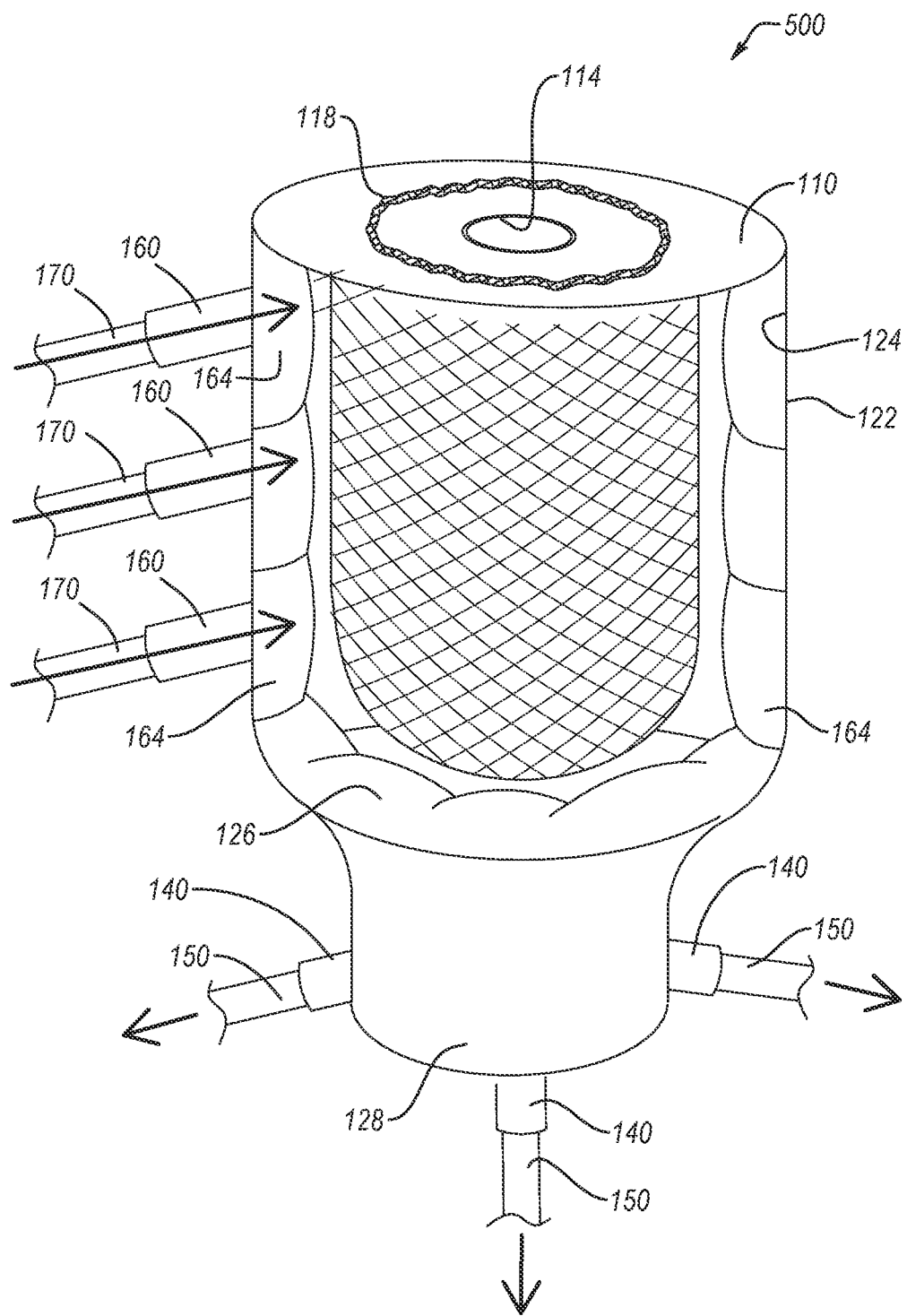
FIG. 5 is an isometric view of a bodily waste collection device, according to an embodiment.

The controller 195 may be used to selectively control the positive pressure source 190 to periodically input fluid and to control application of vacuum by the vacuum source 185 to create peristaltic motion within the bodily waste collection device. FIG. 5 is an isometric view of a bodily waste collection device 500, according to an embodiment. The bodily waste collection device 500 may be similar or identical to the bodily waste collection device 101, in one or more aspects. For example, the bodily waste collection device 500 includes the annular body 110, the fluid impermeable barrier 120, the filter bag 130, the one or more ports 140, and the at least one input port 160. The bodily waste collection device 500 includes one or more bladders 164 disposed longitudinally in the chamber, such as longitudinally (e.g., in a longitudinal series) along the inner surface 124 of the fluid impermeable barrier 120. The one or more bladders 164 may be disposed circumferentially around the inner surface 124 and the filter bag 130. The one or more bladders 164 may have at least one input port 160 fluidly connected thereto. For example, each bladder of the one or more bladders 164 may have an input port 160 fluidly coupled thereto. Accordingly, fluid input via the at least one input port 160 may at least partially fill the one or more bladders 164 to provide inward pressure to the contents of the chamber 126.

Each bladder of the one or more bladders 164 may be selectively filled with fluid (e.g., air or liquid), such as sequentially, to mimic peristalsis within the chamber 126. In some examples, each bladder may be independently filled by the positive pressure source.

In some examples (not shown), the one or more bladders 164 may be fluidly connected to each other via connections or valves therebetween. In such example, only a single input port 160 may be fluidly connected to an uppermost bladder (e.g., closest to the opening 114) of the one or more bladders 164. The one or more bladders may be at least partially inflated via input into the uppermost (e.g., first) bladder, which input progressively flows into each subsequent bladder. Accordingly, the one or more bladders 164 may be selectively filled to mimic peristalsis.

The fluid input into the one or more bladders 164 may include air or a liquid. By utilizing the one or more bladders, liquid may be used without causing the liquid to contact the bodily waste. In such examples, the liquid may be temperature controlled. For example, the liquid may be heated or cooled to a selected temperature by the positive pressure source, such as for comfort for the wearer.

The controller 195 (FIG. 1) may include machine readable and executable instructions to selectively inflate and deflate the one or more bladders 164 (e.g., plurality of bladders), such as sequentially to create peristaltic motion in the chamber.

Figure 6:
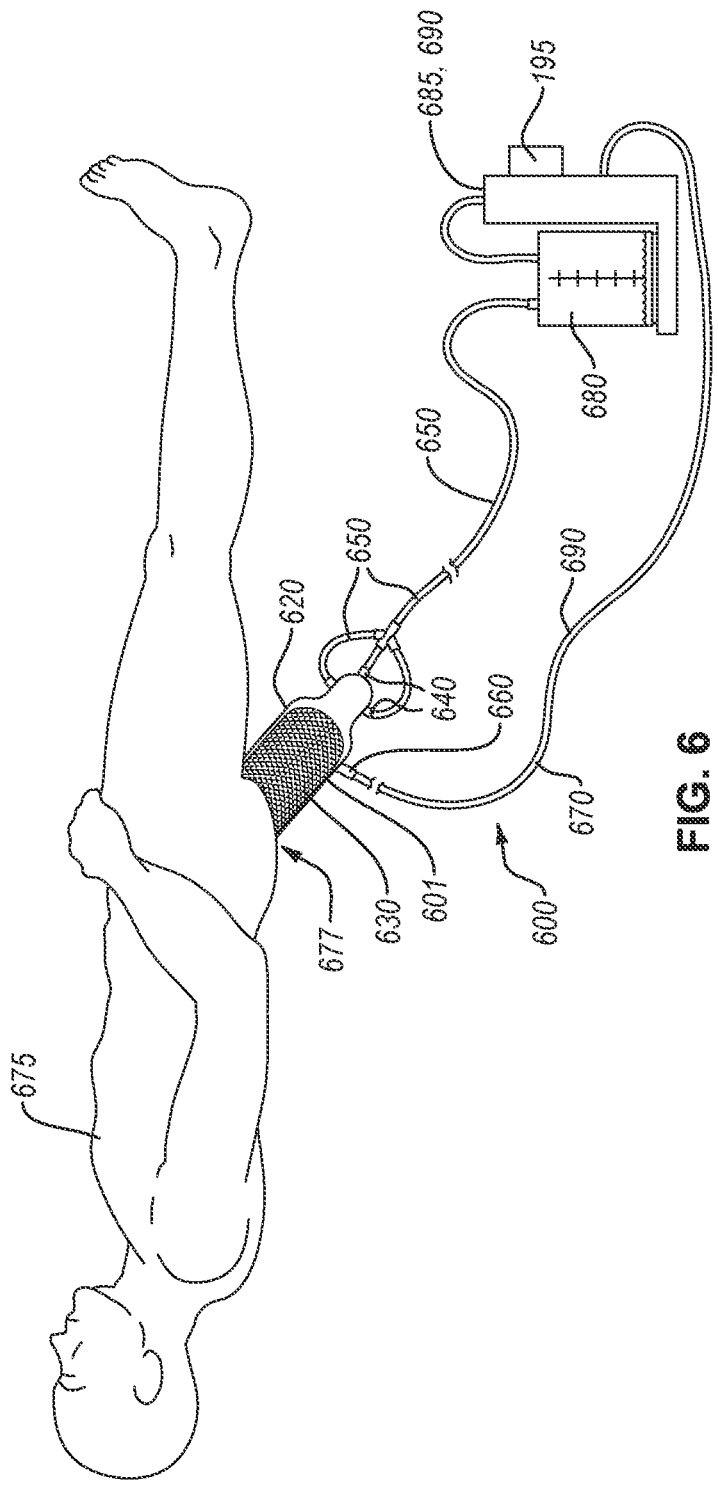
FIG. 6 is a schematic of the bodily waste collection system during use, according to an embodiment.

FIG. 6 is a schematic of the bodily waste collection system 600 during use, according to an embodiment. The bodily waste collection system 600 includes the bodily waste collection device 601, the fluid storage container 680, the vacuum source 685, the positive pressure source 690, and the controller 195. the bodily waste collection device 601 may be similar or identical to any of the bodily waste collection devices disclosed herein. For example, the bodily waste collection device 601 may include the annular body (not shown), the fluid impermeable barrier 620, the filter bag 630, the one or more ports 640, and the at least one input port 660.

The bodily waste collection device 601 is fluidly connected to the vacuum source 685 via the one or more ports 640 and the drainage tubing 650. The bodily waste collection device 601 may be fluidly connected to the vacuum source 685 via the fluid storage container 680. The bodily waste collection device 601 is fluidly connected to the positive pressure source 690 via the at least one input port 660 and the one or more input tubes 670.

The vacuum source 685 may be similar or identical to any of the vacuum sources disclosed herein, in one or more aspects. The positive pressure source 690 may be similar or identical to any of the positive pressure sources disclosed herein, in one or more aspects. As shown, the vacuum source 685 and the positive pressure source 690 may be located in a single device. The controller 195 may be operably coupled to the vacuum source 685 and the positive pressure source 690 to selectively control each.

The bodily waste collection device 601 may be positioned on the wearer 675, such as within the gluteal cleft 677 of the wearer 675. The bodily waste collection device 601 may be similar or identical any of the bodily waste collection devices disclosed herein. The annular body of the bodily waste collection device 601 may be positioned around the anus of the wearer 675 such that the opening (not shown) of the annular body (not shown) is disposed over the anus of the wearer 675. At least a portion of the bodily waste collection device 601 may be retained within the gluteal cleft 677 of the wearer 675. For example, the annular body may be adhered to the skin of the wearer 675 around the anus and when the wearer's legs are closed, the annular body will be deformed (e.g., folded) in the gluteal cleft 677.

As the wearer 675 has bowel movements, the waste (e.g., stool) is collected in the filter bag 630 via the opening. The solids are retained in the filter bag 630 while liquid drains from the waste and passes out of the filter bag 630 into the chamber of the bodily waste collection device 601. Such drainage may be accomplished by one or more of gravity or the vacuum applied in the chamber by the vacuum source 685. The liquid is removed from the chamber via the one or more ports and the drainage tubing 650. The liquid is deposited in the fluid storage container 680. The vacuum source 685 may be intermittently controlled to apply a vacuum at selected intervals.

The positive pressure source 690 may be used to periodically input fluid into the chamber to create periodic inward pressure on the contents of the bodily waste collection device 601. The positive pressure source 690 may input one or more fluids into the bodily waste collection device 601 via the input port(s) 660 and the input tube 670. A liquid may be input into the chamber from the positive pressure source as disclosed herein. For example, a stream of air may be passed into the chamber from the positive pressure source 690 to at least partially inflate the fluid impermeable barrier 620 (e.g., the chamber). In some examples, a stream of air or liquid may be passed into the one or more bladders from the positive pressure source 690 to at least partially inflate the fluid impermeable barrier 620. A stream of air may be passed into the chamber from the positive pressure source 690 while the vacuum is applied therein from the vacuum source 685 to prevent the suction from reaching the wearer's tissue (e.g., skin). The fluid may be provided while the vacuum is being applied or while the vacuum is not being applied.

Figure 7:
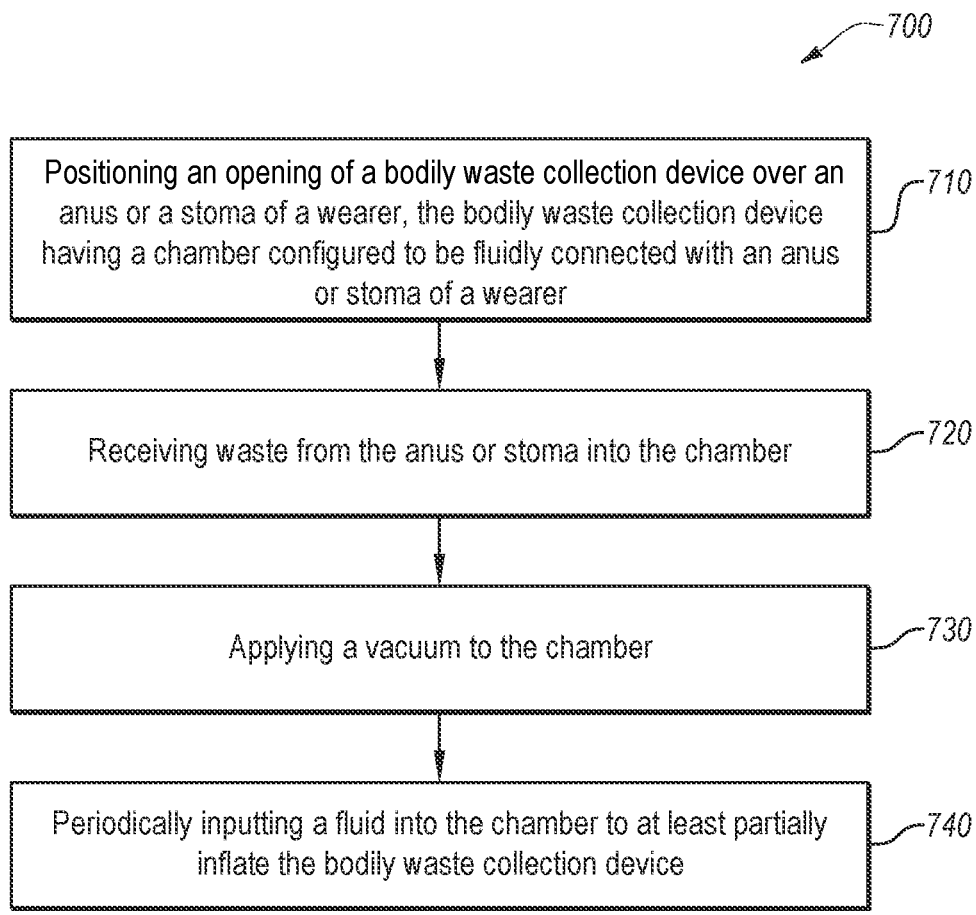
FIG. 7 is a flow diagram of a method to collect bodily waste, according to an embodiment.

FIG. 7 is a flow diagram of a method 700 to collect bodily waste, according to an embodiment. The method 700 includes block 710, which recites "positioning an opening of a bodily waste collection device over an anus or a stoma of a wearer, the bodily waste collection device having a chamber configured to be fluidly connected with an anus or stoma of a wearer." Block 710 may be followed by block 720, which recites "receiving waste from the anus or stoma into the chamber." Block 720 may be followed by block 730, which recites "applying a vacuum to the chamber." Block 730 may be followed by block 740, which recites "periodically inputting a fluid into the chamber to at least partially inflate the bodily waste collection device." Blocks 710, 720, 730, and 740 of the method 700 are for illustrative purposes. For example, the blocks may be modified, supplemented, split, or combined. In an example, one or more of the blocks 710, 720, 730, or 740 of the method 700 may be omitted from the method 700. Any of the blocks 710, 720, 730, or 740 may include using any of the bodily waste collection devices or systems disclosed herein.

Block 710 recites "positioning an opening of a bodily waste collection device over an anus or a stoma of a wearer, the bodily waste collection device having a chamber configured to be fluidly connected with an anus or stoma of a wearer." The bodily waste collection device or components thereof may be similar or identical to any of the bodily waste collection devices disclosed herein, in one or more aspects. For example, the bodily waste collection device may include one or more of an annular body, a fluid impermeable barrier, a filter bag, one or more ports, one or more input tubes, or one or more bladders as disclosed herein.

The bodily waste collection device may include an annular body defining an opening therein, the annular body being configured to be positioned over the anus or stoma of the wearer to position the opening around the anus or the stoma. The bodily waste collection device may include a fluid impermeable barrier affixed to the annular body, the fluid impermeable barrier having an outer surface and an inner surface, the inner surface at least partially defining a chamber within the fluid impermeable barrier. The bodily waste collection device may include a filter bag disposed within the chamber and positioned to receive waste via the opening. The bodily waste collection device may include one or more ports disposed on the fluid impermeable barrier and configured to be attached to a drainage tube.

The bodily waste collection device may form part of a (bodily) waste collection system. The waste collection system may include a fluid storage container configured to hold a fluid. The waste collection system may include a drainage tube in fluid communication with the chamber. The waste collection system may include a vacuum source fluidly coupled to one or more of the fluid storage container or the bodily waste collection device via the drainage tube, the vacuum source configured apply a vacuum to draw fluid from the chamber via the drainage tube. The waste collection system may include a positive pressure source in fluid communication with the chamber, wherein the positive pressure source is configured to periodically input fluid into the chamber to create inward pressure (e.g., peristaltic motion) in combination with the vacuum. The waste collection system may include one or more input tubes in fluid communication with the chamber and the positive pressure source.

Positioning the opening of the bodily waste collection device over the anus or stoma of a wearer may include positioning the opening over the anus or stoma such that the opening at least partially (e.g., completely) encircles the anus or stoma. Accordingly, bodily waste passed through the anus or stoma may pass through the opening into the bodily waste collection device. Positioning the opening of the bodily waste collection device over the anus or stoma of a wearer may include adhering the annular body to the wearer, such as in the intergluteal cleft of the wearer. Positioning the opening of the bodily waste collection device over the anus or stoma of a wearer may include deforming a conformation of the annular body to comply with the anatomy of the wearer around the anus or stoma, such as by one or more of bending or folding. The wearer or a user (e.g., caretaker, medical professional, etc.) may position the opening of the bodily waste collection device over the anus or stoma of a wearer Block 720 recites "receiving waste from the anus or stoma into the chamber." For example, receiving waste from the anus or stoma into the chamber includes receiving the waste into chamber via the opening. Receiving waste from the anus or stoma into the chamber may include receiving the waste into the filter bag. Receiving waste from the anus or stoma into the chamber may include retaining the solids of the waste in the filter bag.

Block 730 recites, "applying a vacuum to the chamber." Applying a vacuum to the chamber may include utilizing any of the vacuum sources disclosed herein. Applying vacuum in the chamber may include applying the vacuum via the one or more ports, such as through a single port or a plurality of ports. Applying a vacuum to the chamber may include removing liquid from the waste in the chamber via the one or more ports. Applying vacuum in the chamber may include applying the vacuum indirectly via the fluid storage container.

Applying vacuum in the chamber may include removing gas from the chamber effective to cause the inner surface of the fluid impermeable barrier to apply inward pressure against the contents (e.g., bodily waste) within the chamber. The vacuum may be maintained for a selected duration, such as any of the durations disclosed herein. Applying vacuum in the chamber may include applying the vacuum intermittently according to any of the intervals disclosed herein for any of the durations disclosed herein. For example, applying the vacuum intermittently may include applying the vacuum at least every hour or at least every 20 minutes. Applying vacuum in the chamber may include applying the vacuum intermittently, such as between input of fluid into the chamber. Applying vacuum in the chamber may include applying the vacuum at a pressure of at least 50 kPa.

Block 740 recites, "periodically inputting a fluid into the chamber to at least partially inflate the bodily waste collection device." Periodically inputting a fluid into the chamber to at least partially inflate the bodily waste collection device may include utilizing any of the input ports, input tubes, and positive pressure sources disclosed herein, such as a gas source or liquid source. Periodically inputting a fluid into the chamber to at least partially inflate the bodily waste collection device may include inputting the fluid into the chamber at any of the frequencies (e.g., at least once per hour) or for any of the durations disclosed herein. For example, periodically inputting a fluid into the chamber to at least partially inflate the bodily waste collection device may include periodically inputting air into the chamber for a selected duration. In some examples, periodically inputting a fluid into the chamber to at least partially inflate the bodily waste collection device includes inputting the fluid at least every hour for the selected duration. Periodically inputting a fluid into the chamber to at least partially inflate the bodily waste collection device may include inputting a gas into the chamber, such as air, oxygen, nitrogen, or the like. In some examples, the positive pressure source may include an air pump and periodically inputting a fluid into the chamber to at least partially inflate the bodily waste collection device includes inputting air into chamber with the air pump.

Inputting fluid (e.g., gas or liquid) into the chamber may be carried out to at least partially inflate one or more bladders in the fluid impermeable barrier of the bodily waste collection device. Such inflation may be carried out in sequence to mimic peristaltic motion as disclosed herein. The fluid may be provided to the one or more bladders (e.g., longitudinally arranged about the chamber) separately or may be provided via a first bladder which is fluidly coupled to one or more subsequent bladders in series where the fluid provided to the first bladder sequentially fills and drains from the subsequent bladders. The fluid input into the bladders provides inward pressure on the contents of the chamber, such as to mimic peristaltic motion within the chamber.

Inputting gas into the chamber may also be carried out to prevent vacuum applied into the chamber from reaching the tissue of the wearer. For example, inputting the gas into the chamber may be carried out contemporaneously with (e.g., simultaneously or close in time to) applying a vacuum in the chamber. Some of the one or more input port(s) may be disposed at a point in the fluid impermeable barrier nearer the wearer than the one or more (drainage) ports. Accordingly, the suction from the drainage ports may be prevented from reaching the wearer by inputting gas into the chamber nearer the wearer.

Periodically inputting a fluid into the chamber to at least partially inflate the bodily waste collection device may include inputting liquid into the chamber, such as water, saline, or the like. Inputting liquid into the chamber may include inputting liquid into one or more bladders to provide an inward force on the contents of the fluid impermeable barrier, such as to mimic peristalsis.

One or both of applying vacuum or periodically inputting a fluid into the chamber may be carried out by manually controlling the vacuum source and the positive pressure source or may be carried out using the controller. For example, applying a vacuum to the chamber and periodically inputting a fluid into the chamber to at least partially inflate the bodily waste collection device may include utilizing the controller to selectively apply the vacuum and periodically input the fluid into the chamber to at least partially inflate the chamber, such as to mimic peristalsis. The controller may include instructions to inflate and deflate the plurality of bladders sequentially, such as to create period inward pressure (e.g., peristaltic motion) in the chamber.

The method 700 may include filtering fluid from the bodily waste with the filter bag. Filtering fluid from the waste with the filter bag may include retaining solids from the waste in the filter bag. Accordingly, semi-solid bodily waste may be filtered in the filter bag to retain the solids therein. In some examples, filtering fluid from the waste with the filter bag includes utilizing gravity to sieve the fluid from the waste. In some examples, filtering fluid from the waste with the filter bag includes utilizing a vacuum to separate the fluid from solids in the waste. For example, the wearer or a user (e.g., medical professional) may visually identify liquid pooling in the chamber or stool in the filter bag through the transparent fluid impermeable barrier, and responsive thereto, activate the vacuum source to remove the liquid from the chamber and/or bodily waste. Filtering fluid from the waste and removing the liquid may be accomplished via block 730 "applying the vacuum to the chamber."

In some examples, the method 700 may include collecting the fluid(s) that are removed from the bodily waste collection device, such as into a fluid storage container that is spaced from the bodily waste collection device and fluidly coupled to the drainage tubing. The fluid storage container may include any of the fluid storage containers disclosed herein. The collected fluid may be quantified or analyzed.

In some examples, the method 700 may include changing the fluid collection device for a new fluid collection device, such as when the filter bag fills with solids. Such a change may be responsive to visually confirming that the filter bag is filled to a point where a change of devices is desired, such as confirming via viewing the filter bag through the transparent fluid impermeable barrier.

Figure 8:
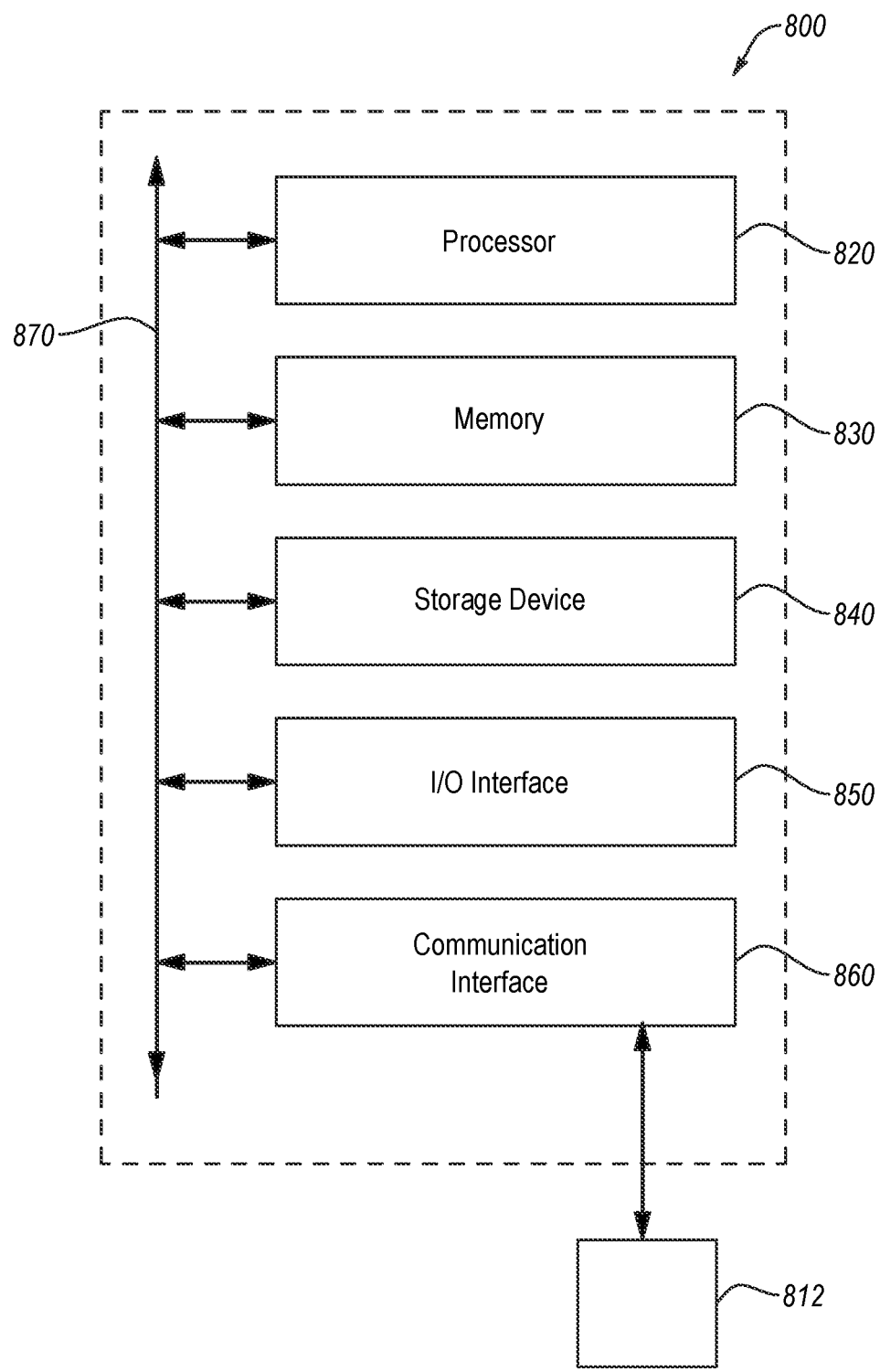
FIG. 8 is a schematic of a controller for executing any of the example methods disclosed herein, according to an embodiment.

Any of the example systems disclosed herein may be used to carry out any of the example methods disclosed herein, such as using the controller 195 shown in FIG. 1. FIG. 8 is a schematic of a controller 800 for executing any of the example methods disclosed herein, according to an embodiment. The controller 800 may be configured to implement any of the example methods disclosed herein, such as the method 700, and may be incorporated into any of the systems disclosed herein such as the system 100 shown in FIG. 1. The controller 800 includes at least one computing device 810. The at least one computing device 810 is an exemplary computing device that may be configured to perform one or more of the acts described above, such as the method 700. The at least one computing device 810 can include one or more servers, one or more computers (e.g., desk-top computer, lap-top computer), one or more mobile computing devices (e.g., smartphone, tablet, etc.), or a proprietary computing device equipped to carry out the acts of the methods disclosed herein. The computing device 810 can comprise at least one processor 820, memory 830, a storage device 840, an input/output ("I/O") device/interface 850, and a communication interface 860. While an example computing device 810 is shown in FIG. 8, the components illustrated in FIG. 8 are not intended to be limiting of the controller 800 or computing device 810. Additional or alternative components may be used in some examples. Further, in some examples, the controller 800 or the computing device 810 can include fewer components than those shown in FIG. 8. For example, the controller 800 may not include the one or more additional computing devices 812. In some examples, the at least one computing device 810 may include a plurality of computing devices, such as a server farm, computational network, or cluster of computing devices. Components of computing device 810 shown in FIG. 8 are described in additional detail below.

In some examples, the processor(s) 820 includes hardware for executing machine readable and executable instructions (e.g., instructions for carrying out one or more portions of any of the methods disclosed herein), such as those making up a computer program. For example, to execute instructions, the processor(s) 820 may retrieve (or fetch) the instructions from an internal register, an internal cache, the memory 830, or a storage device 840 and decode and execute them. In particular examples, processor(s) 820 may include one or more internal caches for data such as look-up tables. As an example, the processor(s) 820 may include one or more instruction caches, one or more data caches, and one or more translation lookaside buffers (TLBs). Instructions in the instruction caches may be copies of instructions in memory 830 or storage device 840. In some examples, the processor 820 may be configured (e.g., include programming stored thereon or executed thereby) to carry out one or more portions of any of the example methods disclosed herein.

In some examples, the processor 820 is configured to perform any of the acts disclosed herein such as in method 700 or cause one or more portions of the computing device 810 or controller 800 to perform at least one of the acts disclosed herein. Such configuration can include one or more operational programs (e.g., computer program products) that are executable by the at least one processor 820. For example, the processor 820 may be configured to initiate, terminate, or automatically adjust application of vacuum from the vacuum source or input from the positive pressure source.

The at least one computing device 810 (e.g., a server) may include at least one memory storage medium (e.g., memory 830 and/or storage device 840). The computing device 810 may include memory 830, which is operably coupled to the processor(s) 820. The memory 830 may be used for storing data, metadata, and programs for execution by the processor(s) 820. The memory 830 may include one or more of volatile and non-volatile memories, such as Random Access Memory (RAM), Read Only Memory (ROM), a solid state disk (SSD), Flash, Phase Change Memory (PCM), or other types of data storage. The memory 830 may be internal or distributed memory.

The computing device 810 may include the storage device 840 having storage for storing data or instructions. The storage device 840 may be operably coupled to the at least one processor 820. In some examples, the storage device 840 can comprise a non-transitory memory storage medium, such as any of those described above. The storage device 840 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 840 may include removable or non-removable (or fixed) media. Storage device 840 may be internal or external to the computing device 810. In some examples, storage device 840 may include non-volatile, solid-state memory. In some examples, storage device 840 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some examples, one or more portions of the memory 830 and/or storage device 840 (e.g., memory storage medium(s)) may store one or more machine readable and executable instructions for carrying out any of the acts disclosed herein.

The computing device 810 also includes one or more I/O devices/interfaces 850, which are provided to allow a user to provide input to, receive output from, and otherwise transfer data to and from the computing device 810. These I/O devices/interfaces 850 may include a mouse, keypad or a keyboard, a touch screen, camera, optical scanner, network interface, web-based access, modem, a port, other known I/O devices or a combination of such I/O devices/interfaces 850. The touch screen may be activated with a stylus or a finger.

The I/O devices/interfaces 850 may include one or more devices for presenting output to a user, including, but not limited to, a graphics engine, a display (e.g., a display screen or monitor), one or more output drivers (e.g., display drivers), one or more audio speakers, and one or more audio drivers. In certain examples, I/O devices/interfaces 850 are configured to provide graphical data to a display for presentation to a user. The graphical data may be representative of one or more graphical user interfaces and/or any other graphical content as may serve a particular implementation.

The computing device 810 can further include a communication interface 860. The communication interface 860 can include hardware, software, or both. The communication interface 860 can provide one or more interfaces for communication (such as, for example, packet-based communication) between the computing device 810 and one or more of the vacuum source (not shown), the positive pressure source (not shown), one or more additional computing devices 812, or one or more networks. For example, communication interface 860 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 860 may be used. For example, computing device 810 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of controller 800 or computing device 810 may communicate with a wireless PAN (WPAN) (such as, for example, a BLUETOOTH® WPAN), a WI-FI network, a WI-MAX network, a cellular telephone network (such as, for example, a Global System for Mobile Communications (GSM) network), or other suitable wireless network or a combination thereof. Computing device 810 may include any suitable communication interface 860 for any of these networks, where appropriate.

The computing device 810 may include a bus 870. The bus 870 can include hardware, software, or both that couples components of computing device 810 to each other. For example, bus 870 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

It should be appreciated that any of the examples of acts described herein, such as in the method 700 may be performed by and/or at the controller 800.

While the devices, systems, and methods disclosed herein can be used over a stoma, the devices, systems, and methods disclosed herein may be used to prevent the necessity of ostomy and stoma for removing stool from a patient. As an alternative to an ostomy, the bodily waste collection devices disclosed herein may be used to non-intrusively and hygienically receive bodily waste from patients. Additionally, the useful life of the devices may be lengthened by removing the fluids from the bodily waste received therein, which is possible by retaining the solids from the waste within the filter bag.

While various aspects and embodiments have been disclosed herein, other aspects and embodiments are contemplated. The various aspects and embodiment disclosed herein are for purposes of illustration and are not intended to be limiting. Features from any of the disclosed embodiments may be used in combination with one another, without limitation.

What is claimed is:

1. A bodily waste collection system, comprising: a fluid storage container configured to hold a fluid; a bodily waste collection device fluidly coupled to the fluid storage container, the bodily waste collection device having a chamber configured to be fluidly connected with an anus or stoma of a wearer; a drainage tubing in fluid communication with the chamber; a vacuum source fluidly coupled to one or more of the fluid storage container or the bodily waste collection device via the drainage tubing, the vacuum source configured to apply a vacuum to draw fluid from the chamber via the drainage tubing; a positive pressure source in fluid communication with the chamber, wherein the positive pressure source is configured to periodically input fluid into the chamber to create periodic pressure in the chamber in combination with the vacuum; and one or more input tubes fluidly connecting the chamber with the positive pressure source; and a controller operably coupled to the positive pressure source and the vacuum source, wherein the controller is configured to selectively control the positive pressure source to regularly input fluid into the chamber at least once per hour, and to control application of vacuum by the vacuum source, to create periodic pressure within the bodily waste collection device.

2. The bodily waste collection system of claim 1 wherein the bodily waste collection device includes at least one input port configured to be connected to the one or more input tubes.

3. The bodily waste collection system of claim 1 wherein:
   the bodily waste collection device includes a fluid impermeable barrier, the fluid impermeable barrier having an outer surface and an inner surface, the inner surface at least partially defining the chamber; and
   at least one input port located in an upper portion of the fluid impermeable barrier.

4. The bodily waste collection system of claim 1 wherein the positive pressure source includes an air pump configured to input air into the chamber via the one or more input tubes.

5. The bodily waste collection system of claim 1 wherein the vacuum source and positive pressure source are located in a single device.

6. The bodily waste collection system of claim 1 wherein the bodily waste collection device includes:
   an annular body defining an opening therein, the annular body being configured to be positioned over the anus or the stoma of the wearer to position the opening around the anus or the stoma;
   a fluid impermeable barrier affixed to the annular body, the fluid impermeable barrier having an outer surface and an inner surface, the inner surface at least partially defining the chamber within the fluid impermeable barrier;
   a filter bag disposed within the chamber and positioned to receive waste via the opening; and
   one or more ports disposed on the fluid impermeable barrier and configured to be attached to the drainage tubing.

7. The bodily waste collection system of claim 6 wherein the annular body is sized and shaped to fit within an intergluteal cleft of the wearer and includes an adhesive disposed on an outward facing surface at least partially around the opening.

8. The bodily waste collection system of claim 6 wherein the filter bag includes a mesh bag having a sieve size selected to allow fluids to pass therethrough and retain solids therein.

9. The bodily waste collection system of claim 6 wherein the one or more ports are disposed in a lower region of the fluid impermeable barrier.

10. A bodily waste collection system, comprising: a fluid storage container configured to hold a fluid; a bodily waste collection device fluidly coupled to the fluid storage container, the bodily waste collection device including: an annular body defining an opening therein, the annular body being configured to be positioned over an anus or stoma of a wearer to position the opening around the anus or the stoma; a fluid impermeable barrier affixed to the annular body, the fluid impermeable barrier having an outer surface and an inner surface, the inner surface at least partially defining a chamber within the fluid impermeable barrier; a filter bag disposed within the chamber and positioned to receive waste via the opening; and one or more ports disposed on the fluid impermeable barrier; a drainage tubing in fluid communication with the chamber via the one or more ports; a vacuum source fluidly coupled to one or more of the fluid storage container or the bodily waste collection device via the drainage tubing, the vacuum source being configured to apply a vacuum to draw fluid from the chamber via the drainage tubing; a positive pressure source in fluid communication with the chamber, wherein the positive pressure source is configured to periodically input fluid into the chamber to create periodic pressure in the chamber in combination with the vacuum; one or more input tubes fluidly connecting the chamber with the positive pressure source; and a controller operably coupled to the positive pressure source and the vacuum source, wherein the controller is configured to selectively control the positive pressure source to regularly input fluid into the chamber, and to control application of vacuum by the vacuum source, to create periodic pressure within the bodily waste collection device.

11. The bodily waste collection system of claim 10 wherein the controller is configured to cause the positive pressure source to input fluid into the chamber at least once per hour.

12. The bodily waste collection system of claim 10 wherein the positive pressure source includes an air pump.

13. The bodily waste collection system of claim 12 wherein the controller is configured to cause the air pump to at least partially inflate the fluid impermeable barrier at least once per hour.

14. The bodily waste collection system of claim 10 wherein the controller is configured to:
cause the vacuum source to apply the vacuum intermittently; and
cause the positive pressure source to periodically input the fluid into the chamber to at least partially inflate the bodily waste collection device includes periodically inputting air into the chamber for a selected duration.

15. The bodily waste collection system of claim 14 wherein the duration is at least 1 minute.

16. The bodily waste collection system of claim 10 wherein:
the bodily waste collection device includes one or more bladders disposed on the fluid impermeable barrier circumferentially around at least a portion of the filter bag; and
the positive pressure source is fluidly connected to the one or more bladders.

17. The bodily waste collection system of claim 16 wherein:
the one or more bladders includes a plurality of bladders arranged longitudinally in the chamber; and
the one or more input tubes include a plurality of input tubes, each connected to a separate bladder of the plurality of bladders.

18. The bodily waste collection system of claim 17 wherein the controller is configured to inflate and deflate the plurality of bladders sequentially to create periodic pressure in the chamber.

* * * * *